US009629834B2

(12) United States Patent
Aoki et al.

(10) Patent No.: US 9,629,834 B2
(45) Date of Patent: Apr. 25, 2017

(54) MEDICINAL COMPOSITION FOR INHIBITING FORMATION AND/OR ENLARGEMENT OF CEREBRAL ANEURYSM OR SHRINKING SAME

(71) Applicants: KYOTO UNIVERSITY, Kyoto-shi (JP); ASTELLAS PHARMA INC., Chuo-ku (JP)

(72) Inventors: Tomohiro Aoki, Kyoto (JP); Ichiro Aramori, Chuo-ku (JP); Jun Hirose, Chuo-ku (JP); Rie Yamamoto, Chuo-ku (JP)

(73) Assignees: KYOTO UNIVERSITY, Kyoto-shi (JP); ASTELLAS PHARMA INC., Chuo-ku (JP)

( * ) Notice: Subject to any disclaimer, the term of this patent is extended or adjusted under 35 U.S.C. 154(b) by 0 days.

(21) Appl. No.: 14/787,197

(22) PCT Filed: Apr. 22, 2014

(86) PCT No.: PCT/JP2014/061335
§ 371 (c)(1),
(2) Date: Oct. 26, 2015

(87) PCT Pub. No.: WO2014/175287
PCT Pub. Date: Oct. 30, 2014

(65) Prior Publication Data
US 2016/0113917 A1  Apr. 28, 2016

(30) Foreign Application Priority Data

Apr. 26, 2013  (JP) ................................ 2013-093747

(51) Int. Cl.
*A61K 31/397* (2006.01)
*A61K 31/453* (2006.01)
*A61K 31/135* (2006.01)
*A61K 31/4245* (2006.01)
*A61K 31/145* (2006.01)

(52) U.S. Cl.
CPC .......... *A61K 31/453* (2013.01); *A61K 31/135* (2013.01); *A61K 31/145* (2013.01); *A61K 31/397* (2013.01); *A61K 31/4245* (2013.01)

(58) Field of Classification Search
CPC .................................................... A61K 31/397
USPC .................................................... 514/210.17
See application file for complete search history.

(56) References Cited

U.S. PATENT DOCUMENTS

| 7,678,820 | B2 | 3/2010 | Harada et al. |
| 7,951,825 | B2 | 5/2011 | Harada et al. |
| 8,193,378 | B2 | 6/2012 | Harada et al. |
| 8,324,283 | B2 * | 12/2012 | Oomura ............... A61K 9/2018 514/649 |
| 8,791,159 | B2 | 7/2014 | Nakade et al. |
| 2005/0009786 | A1 | 1/2005 | Pan et al. |
| 2007/0248944 | A1 | 10/2007 | Yoshimura et al. |
| 2008/0039530 | A1 | 2/2008 | Hla et al. |
| 2010/0068705 | A1 | 3/2010 | Helgadottir et al. |
| 2011/0092484 | A1 | 4/2011 | Hashimoto et al. |
| 2012/0178735 | A1 | 7/2012 | Harada et al. |
| 2014/0288034 | A1 | 9/2014 | Nakade et al. |

FOREIGN PATENT DOCUMENTS

| JP | 2003 104894 | 4/2003 |
| JP | 2006 89455 | 4/2006 |
| JP | 2007 503468 | 2/2007 |
| JP | 2007 523858 | 8/2007 |
| JP | 2008 19221 | 1/2008 |
| JP | 2009 107955 | 5/2009 |
| JP | 2010 518848 | 6/2010 |
| WO | 2005 020882 | 3/2005 |
| WO | 2006 022281 | 3/2006 |
| WO | 2007 116866 | 10/2007 |
| WO | 2008 149971 | 12/2008 |
| WO | 2010 064707 | 6/2010 |
| WO | 2011 007565 | 1/2011 |

OTHER PUBLICATIONS

Hasegawa et al., Stroke Feb. 2010 41(2): 368-374.*
Juvela et al., Stroke Feb. 2001 32: 485-491.*
Written Opinion issued Aug. 5, 2014 in PCT/JP2014/061335 (submitting English translation only).
Extended European Search Report issued Oct. 10, 2016 in Patent Application No. 14788085.0.
Orhan Altay, et al., "Isoflurane delays the development of early brain injury after subarachnoid hemorrhage through sphingosine-related pathway activation in mice," Elsevier Science Publishers, XP002762282, Jun. 2012, pp. 1-15. (with English abstract).
Martin H. Bolli, et al., "Synthetic Sphingosine 1-Phosphate Receptor Modulators—Opportunities and Potential Pitfalls," Current Topics in Medicinal Chemistry, vol. 11, No. 6, XP55110362, (2011), pp. 726-757.
International Search Report Issued Aug. 5, 2014 in PCT/2014/061335 filed Apr. 22, 2014.
Omori, K. et al., "Edaravone mimics sphingosine-1-phosphate-induced endothelial barrier enhancement in human microvascular endothelial cells", Am. J.Physiol. Cell Physiol., vol. 293, pp. C1523-1531, 2007.
Takahashi, M. et al., "Lipid Mediator Sphingosine-1-Phosphate(S1P): Efficacy of Novel S1P Receptor Agonists in the Treatment of Autoimmune Diseases", The Shinshu Medical Journal, vol. 57, No. 4, pp. 127-136, 2009.

(Continued)

*Primary Examiner* — Yong Chu
*Assistant Examiner* — Sonya Wright
(74) *Attorney, Agent, or Firm* — Oblon, McClelland, Maier & Neustadt, L.L.P.

(57) ABSTRACT

Provided is a pharmaceutical composition which enables the inhibition of formation and/or enlargement of cerebral aneurysm or the regression of cerebral aneurysm. The pharmaceutical composition for the inhibition of formation and/or enlargement of cerebral aneurysm or for the regression of cerebral aneurysm of the present invention, which includes a $S1P_1$ receptor agonist as an active ingredient, enables the inhibition of formation and/or enlargement of cerebral aneurysm or the regression of cerebral aneurysm, and enables the prevention and/or treatment of a disease associated with cerebral aneurysm.

4 Claims, 8 Drawing Sheets

(56) References Cited

OTHER PUBLICATIONS

Krishna, S. M. et al., "Fenofibrate Increases High-Density Lipoprotein and Sphingosine 1 Phosphate Concentrations Limiting Abdominal Aortic Aneurysm Progression in a Mouse Model", The American Journal of Pathology, vol. 181, No. 2, pp. 706-718, 2012.

Takeuchi, S. et al., "Flow patterns and distributions of fluid velocity and wall shear stress in the human internal carotid and middle cerebral arteries", World Neurosurgery, vol. 73, No. 3, pp. 174-185, 2010.

Meng, H. et al., "Complex Hemodynamics at the Apex of an Arterial Bifurcation Induces Vascular Remodeling Resembling Cerebral Aneurysm Initiation", Hemodynamics at Bifurcation Induces Aneurysm, vol. 38, No. 6, pp. 1924-1931, 2007.

Nakatani, H. et al., "Cerebral blood flow patterns at major vessel bifurcations and aneurysms in arts", Journal of Neurosurgery, vol. 74, No. 2, pp. 258-262, 1991.

Wang, Z. et al., "Molecular Alterations Associated with Aneurysmal Remodeling are Localized in the High Hemodynamic Stress Region of a Created Carotid Bifurcation", Neurosurgery, vol. 65, No. 1, pp. 169-178, 2009.

Kataoka, H. et al., "Molecular basis for the development of intracranial aneurysm", Expert Review of Neurotherapeutics, vol. 10, No. 2, pp. 173-187, 2010.

Seikagaku, The Journal of Japanese Biochemical Society, vol. 83, No. 6, pp. 536-544, 2011, (with Partial English translation).

Lin, Chi-Iou et al., "Sphingosine 1-phosphate regulates inflammation-related genes in human endothelial cells through S1P1 and S1P3", Biochemical and Biophysical Research Communications, vol. 355, pp. 895-901, 2007.

Hughes, J. E. et al., "Sphingosine-1-Phosphate Induces an Antiinflammatory Phenotype in Macrophages", Circulation Research, vol. 102, No. 8, pp. 950-958, 2008.

Jung, B. et al., "Flow-Regulated Endothelial S1P Receptor-1 Signaling Sustains Vascular Development", Developmental Cell, vol. 23, No. 3, pp. 600-610, 2012.

\* cited by examiner

Figure 1

ANTI-S1P1 ANTIBODY: MURINE MONOCLONAL ANTIBODY
(Millipore MABC94)

Figure 2

NUMERICAL NUMBERS SHOWN IN THE GRAPH EACH REPRESENT
% RELATIVE TO THE VEHICLE GROUP.
**: $p<0.01$

A: BLOOD PRESSURE

B: HEART RATE

MEDICINAL COMPOSITION FOR INHIBITING FORMATION AND/OR ENLARGEMENT OF CEREBRAL ANEURYSM OR SHRINKING SAME

CROSS REFERENCE TO RELATED APPLICATION

This application is a National Stage entry under 35 USC 371 of PCT/JP2014/061335 filed on Apr. 22, 2014, and claims priority to Japanese Patent Application No. No. 2013-093747 filed on Apr. 26, 2013.

TECHNICAL FIELD

The present invention relates to a pharmaceutical composition for the inhibition of formation and/or enlargement of cerebral aneurysm or for the regression of cerebral aneurysm, and also relates to a pharmaceutical composition for the prevention and/or treatment of a disease associated with cerebral aneurysm.

The present application claims priority from Japanese Patent Application No. 2013-093747, which is incorporated herein by reference.

BACKGROUND ART

Cerebral aneurysm is said to be present in 2% to 5% of a general population. In recent years, cases where the presence of cerebral aneurysm is found have rapidly increased along with the spread of a medical checkup of brain or a brain testing. Subarachnoid hemorrhage is a disease mainly caused by rupture of cerebral aneurysm, which has a high mortality, and patients with subarachnoid hemorrhage suffer from severe aftereffects or higher brain dysfunctions in many cases even when the patients survive. In addition, when cerebral aneurysm is found in an unruptured state, a surgical treatment, such as surgical clipping involving craniotomy and coil embolization, is conducted at present as a method for prevention of the rupture of cerebral aneurysm. Such surgical treatment is severely burdensome for patients and a surgical risk is often higher than the risk of the rupture of untreated aneurysm, and therefore the development of noninvasive pharmacotherapy has been desired. Hitherto, there have been several reports on the possibility of pharmacotherapy (Patent documents 1 to 5 and the like), but there has not yet been any established drug therapy. Thus, a drug for the inhibition of formation and/or enlargement of cerebral aneurysm or for the regression of cerebral aneurysm has been desired.

The mechanism of formation of cerebral aneurysm has not yet been sufficiently elucidated. However, for example, it has been reported that high hemodynamic stress conditions are observed at human cerebral aneurysm development sites (Non-Patent document 1), and cerebral aneurysm is induced in a rat by applying high hemodynamic stress (Non-Patent documents 2 and 3). In addition, it has been reported that, in experimentally induced cerebral aneurysm, vascular remodeling occurs at the site to which high hemodynamic stress is applied (Non-Patent document 4). Based on those reports, it has been speculated that cerebral aneurysm is a disease which is induced by hemodynamic stress. Further, it has been thought that the dysfunction of vascular endothelial cells, apoptosis, inflammation, and the like play important roles in the process of formation of cerebral aneurysm. In Non-Patent document 5, for example, it has been reported that endothelial nitric oxide synthase (eNOS) and tumor necrosis factor-α (TNF-α) are involved in the dysfunction of vascular endothelial cells, TNF-α is involved in apoptosis, and the activation of nuclear factor kappa B (NF-κB) by TNF-α, monocyte chemotactic protein-1 (MCP-1), and vascular cell adhesion protein 1 (VCAM-1) is involved in inflammation.

Incidentally, sphingosine 1-phosphate (hereinafter referred to as "SIP") is one kind of lipid mediator which is produced in the process of the metabolism of sphingolipids and which acts on various cells. A SIP receptor is a G-protein-coupled receptor and five subtypes of the SIP receptor ($S1P_1$ receptor to $S1P_5$ receptor) have been identified. All of these receptors are broadly distributed in cells and tissues throughout the body, but the $S1P_1$ receptor, the $S1P_3$ receptor, and the $S1P_4$ receptor are predominantly expressed in lymphocytes and vascular endothelial cells, the $S1P_2$ receptor is predominantly expressed in vascular smooth muscle cells, and the $S1P_5$ receptor is predominantly expressed in brain and spleen, and amino acid sequences thereof are well conserved among humans and rodents. SIP and its receptors are essential for formation and development of nascent blood vessels and nervous systems, and are involved in immune functions in vivo. Further, it has been found that, also in the cardiovascular system, SIP is involved in the barrier function of endothelial cells, angiogenesis, arteriosclerosis, and vascular and myocardial remodeling (Non-Patent document 6).

A $S1P_1$ receptor agonist is known to induce the down-regulation of the $S1P_1$ receptor on lymphocytes and to inhibit the $S1P_1$ receptor-dependent transfer of lymphocytes from secondary lymphoid tissues in immunoreactions involving lymphocytes. Therefore, the $S1P_1$ receptor agonist is expected to exhibit effectiveness in the prevention or treatment of a disease caused by undesired lymphocyte infiltration, for example, transplant rejection of organs, bone marrow, or tissues, an autoimmune disease, such as rheumatoid arthritis, and multiple sclerosis, and an inflammatory disease, such as cerebrospinal meningitis, hepatitis and inflammatory bowel disease, and a large number of compounds each serving as the $S1P_1$ receptor agonist have been reported (Patent documents 6, 7, and 8 and the like). In Patent document 8, there are listed a large number of diseases, as diseases involving EDG-1 ($S1P_1$), for example, varicose vein, such as hemorrhoid, anal fissure and anal fistula, and dissecting aneurysm, but there is no disclosure of cerebral aneurysm.

Meanwhile, there are also various reports on in vivo roles of the signaling via the S1P receptor. With regard to the relationship between the S1P receptor and inflammatory substances regulated via the S1P receptor, it has been reported that S1P increases mRNAs of IL-8 and MCP-1, which are involved in inflammation via the $S1P_1$ receptor and the $S1P_3$ receptor in normal human umbilical vein endothelial cells (HUVECs) (Non-Patent document 7). Meanwhile, it has been reported that S1P inhibits the activation of NF-κB via the $S1P_1$ receptor, and S1P inhibits the expressions of mRNAs of inflammatory substances which are induced by the treatment with lipopolysaccharide (LPS), such as TNFα and MCP-1, in murine macrophages (Non-Patent document 8). In addition, it has been reported that S1P and the $S1P_1$ receptor agonist inhibit LPS-induced TNFα production by murine macrophages, and the inhibitory action of S1P and the $S1P_1$ receptor agonist on the TNFα production is inhibited by a $S1P_1$ receptor antagonist (Non-Patent document 8).

Further, with regard to the roles of the $S1P_1$ receptor expressed in vascular endothelial cells, there is a report suggesting that a signal mediated by the $S1P_1$ receptor enhances adherens junction between cells so that excess buddings of blood vessels are inhibited to stabilize new blood vessels, and besides, the $S1P_1$ receptor plays a role of stabilizing new blood vessels which are activated by responding not only to its ligand S1P, but also to the shear stress of hemodynamic (Non-Patent document 9).

As described above, the mechanism of formation of cerebral aneurysm has not yet been sufficiently elucidated. With regard to a method for the prevention or treatment of enlargement or rupture of cerebral aneurysm, the development of a method which is not performed by a surgical procedure, such as surgical clipping involving craniotomy or coil embolization involving an intravascular surgery, has been desired.

CITATION LIST

Patent Document

[Patent document 1] JP 2009-107955 A
[Patent document 2] WO 2008/149971 A1
[Patent document 3] JP 2008-19221 A
[Patent document 4] JP 2006-89455 A
[Patent document 5] JP 2003-104894 A
[Patent document 6] WO 2007/116866 A1
[Patent document 7] WO 2010/064707 A1
[Patent document 8] WO 2005/020882 A2

Non-Patent Document

[Non-Patent document 1] World Neurosurgery, 2010, Vol. 73(3), pp. 174-185
[Non-Patent document 2] Stroke, 2007, Vol. 38(6), pp. 1924-1931
[Non-Patent document 3] Journal of Neurosurgery, 1991, Vol. 74(2), pp. 258-262
[Non-Patent document 4] Neurosurgery, 2009, Vol. 65(1), pp. 169-178
[Non-Patent document 5] Expert Review of Neurotherapeutics, 2010, Vol. 10(2), pp. 173-187
[Non-Patent document 6] SEIKAGAKU (The Journal of Japanese Biochemical Society), 2011, Vol. 83, No. 6, pp. 536-544
[Non-Patent document 7] Biochemical and Biophysical Research Communications, 2007, Vol. 355, pp. 895-901
[Non-Patent document 8] Circulation Research, 2008, Vol. 102(8), pp. 950-958
[Non-Patent document 9] Developmental Cell, 2012, Vol. 23(3), pp. 600-610

SUMMARY OF INVENTION

Technical Problem

According to one embodiment of the present invention, there is provided a pharmaceutical composition which can inhibit formation and/or enlargement of cerebral aneurysm or can regress cerebral aneurysm. According to another embodiment of the present invention, there is provided a pharmaceutical composition for the prevention and/or treatment of a disease associated with cerebral aneurysm.

Solution to Problem

The inventors of the present invention have conducted intensive investigations by focusing on a $S1P_1$ receptor, and as a result, have found that a $S1P_1$ receptor agonist inhibits formation and enlargement of cerebral aneurysm, thus completed the present invention.

That is, the present invention includes the following.

(1) A pharmaceutical composition for inhibition of formation and/or enlargement of cerebral aneurysm or for regression of cerebral aneurysm, including a sphingosine-1-phosphate receptor 1 agonist as an active ingredient.

(2) The pharmaceutical composition for inhibition of formation and/or enlargement of cerebral aneurysm or for regression of cerebral aneurysmaccordingto Item (1), in which the sphingosine-1-phosphate receptor 1 agonist includes a compound selected from 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof, 1-[(7-{[4-(2,2,2-trifluoroethoxy)-3-(trifluoromethyl)benzyl]oxy}-2H-chromen-3-yl)methyl]piperidine-4-carboxylic acid or a pharmaceutically acceptable salt thereof, 2-amino-2-[2-[4-[3-(benzyloxy)phenylsulfanyl]-2-chlorophenyl]ethyl]propane-1,3-diol or a pharmaceutically acceptable salt thereof, and 1-[4-[N-[4-cyclohexyl-3-(trifluoromethyl)benzyloxy]-1(E)-imino ethyl]-2-ethylbenzyl]azetidine-3-carboxylic acid or a pharmaceutically acceptable salt thereof.

(3) The pharmaceutical composition for inhibition of formation and/or enlargement of cerebral aneurysm or for regression of cerebral aneurysmaccordingto Item (2), in which the sphingosine-1-phosphate receptor 1 agonist includes 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof.

(4) A pharmaceutical composition for prevention and/or treatment of a disease associated with cerebral aneurysm, including a sphingosine-1-phosphate receptor 1 agonist as an active ingredient.

(5) The pharmaceutical composition for prevention and/or treatment according to Item (4), in which the disease associated with cerebral aneurysm includes a disease associated with formation, enlargement, or rupture of cerebral aneurysm.

(6) The pharmaceutical composition for prevention and/or treatment according to Item (5), in which the disease associated with cerebral aneurysm includes subarachnoid hemorrhage.

(7) The pharmaceutical composition according to Item (6), in which the sphingosine-1-phosphate receptor 1 agonist includes a compound selected from 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof, 1-[(7-{[4-(2,2,2-trifluoroethoxy)-3-(trifluoromethyl)benzyl]oxy}-2H-chromen-3-yl)methyl]piperidine-4-carboxylic acid or a pharmaceutically acceptable salt thereof, 2-amino-2-[2-[4-[3-(benzyloxy)phenylsulfanyl]-2-chlorophenyl]ethyl]propane-1,3-diol or a pharmaceutically acceptable salt thereof, and 1-[4-[N-[4-cyclohexyl-3-(trifluoromethyl)benzyloxy]-1(E)-imino ethyl]-2-ethylbenzyl]azetidine-3-carboxylic acid or a pharmaceutically acceptable salt thereof.

(8) The pharmaceutical composition according to Item (7), in which the sphingosine-1-phosphate receptor 1 agonist includes 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof.

(9) Use of a sphingosine-1-phosphate receptor 1 agonist for production of the pharmaceutical composition of Item (1) or (4).

(10) The use of a sphingosine-1-phosphate receptor 1 agonist according to Item (9), in which the sphingosine-1-phosphate receptor 1 agonist includes a compound selected from 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof, 1-[(7-{[4-(2,2,2-trifluoroethoxy)-3-(trifluoromethyl)benzyl]oxy}-2H-chromen-3-yl)methyl]piperidine-4-carboxylic acid or a pharmaceutically acceptable salt thereof, 2-amino-2-[2-[4-[3-(benzyloxy)phenylsulfanyl]-2-chlorophenyl]ethyl]propane-1,3-diol or a pharmaceutically acceptable salt thereof, and 1-[4-[N-[4-cyclohexyl-3-(trifluoromethyl)benzyloxy]-1(E)-imino ethyl]-2-ethylbenzyl]azetidine-3-carboxylic acid or a pharmaceutically acceptable salt thereof.

(11) The use of a sphingosine-1-phosphate receptor 1 agonist according to Item (10), in which the sphingosine-1-phosphate receptor 1 agonist includes 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof.

(12) Use of a pharmaceutical composition including a sphingosine-1-phosphate receptor 1 agonist for the prevention or treatment of a disease associated with cerebral aneurysm.

(13) The use of a pharmaceutical composition for prevention or treatment according to Item (12), in which the disease associated with cerebral aneurysm includes a disease associated with formation, enlargement, or rupture of cerebral aneurysm.

(14) The use of a pharmaceutical composition for prevention or treatment according to Item (13), in which the disease associated with cerebral aneurysm includes subarachnoid hemorrhage.

(15) The use according to Item (12), in which the sphingosine-1-phosphate receptor 1 agonist includes a compound selected from 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof, 1-[(7-{[4-(2,2,2-trifluoroethoxy)-3-(trifluoromethyl)benzyl]oxy}-2H-chromen-3-yl)methyl]piperidine-4-carboxylic acid or a pharmaceutically acceptable salt thereof, 2-amino-2-[2-[4-[3-(benzyloxy)phenylsulfanyl]-2-chlorophenyl]ethyl]propane-1,3-diol or a pharmaceutically acceptable salt thereof, and 1-[4-[N-[4-cyclohexyl-3-(trifluoromethyl)benzyloxy]-1(E)-imino ethyl]-2-ethylbenzyl]azetidine-3-carboxylic acid or a pharmaceutically acceptable salt thereof.

(16) The use according to Item (15), in which the sphingosine-1-phosphate receptor 1 agonist includes 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof.

(17) A method for prevention and/or treatment of a disease associated with cerebral aneurysm, the method including administrating an effective amount of a sphingosine-1-phosphate receptor 1 agonist to a subject.

(18) The method for prevention and/or treatment according to Item (17), in which the sphingosine-1-phosphate receptor 1 agonist includes a compound selected from 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof, 1-[(7-{[4-(2,2,2-trifluoroethoxy)-3-(trifluoromethyl)benzyl]oxy}-2H-chromen-3-yl)methyl]piperidine-4-carboxylic acid or a pharmaceutically acceptable salt thereof, 2-amino-2-[2-[4-[3-(benzyloxy)phenylsulfanyl]-2-chlorophenyl]ethyl]propane-1,3-diol or a pharmaceutically acceptable salt thereof, and 1-[4-[N-[4-cyclohexyl-3-(trifluoromethyl)benzyloxy]-1(E)-imino ethyl]-2-ethylbenzyl]azetidine-3-carboxylic acid or a pharmaceutically acceptable salt thereof.

(19) The method for prevention and/or treatment according to Item (18), in which the sphingosine-1-phosphate receptor 1 agonist includes 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof.

(20) The method for prevention and/or treatment according to Item (18), in which the disease associated with cerebral aneurysm includes a disease associated with formation, enlargement, or rupture of cerebral aneurysm.

(21) The method for prevention and/or treatment according to Item (20), in which the disease associated with cerebral aneurysm includes subarachnoid hemorrhage.

Advantageous Effects of Invention

The pharmaceutical composition for the inhibition of formation and/or enlargement of cerebral aneurysm or for the regression of cerebral aneurysm according to the embodiment of the present invention, which includes a $S1P_1$ receptor agonist as an active ingredient, enables the formation and/or enlargement of cerebral aneurysm or the regression of cerebral aneurysm, without surgical treatments, such as surgical clipping involving craniotomy and coil embolization. In addition, the pharmaceutical composition for the inhibition of formation and/or enlargement of cerebral aneurysm or for the regression of cerebral aneurysm according to the embodiment of the present invention has almost the same influences on blood pressure and heart rate as a group without being administered a drug, and hence has high safety.

Description of Embodiments

The pharmaceutical composition for the inhibition of formation and/or enlargement of cerebral aneurysm or for the regression of cerebral aneurysm according to the present invention includes a sphingosine-1-phosphate receptor 1 agonist ($S1P_1$ receptor agonist) as an active ingredient.

In this specification, the following abbreviations are used in some cases.

Compound 1=5-{5-[3-(trifluoromethyl)-4-{[(2S)-1,1,1-trifluoropropan-2-yl]oxy}phenyl]-1,2,4-oxadiazol-3-yl}-1H-benzimidazole hydrochloride (it should be noted that the compound is also disclosed in WO 2007/116866 A1), Free form of Compound 1=5-{5-[3-(trifluoromethyl)-4-{[(2S)-1,1,1-trifluoropropan-2-yl]oxy}phenyl]-1,2,4-oxadiazol-3-yl}-1H-benzimidazole, Compound 2=1-[(7-{[4-(2,2,2-trifluoroethoxy)-3-(trifluoromethyl)benzyl]oxy}-2H-chromen-3-yl)methyl]piperidine-4-carboxylic acid hydrochloride (it should be noted that the compound is also disclosed in WO 2010/064707 A1), Compound 3=2-amino-2-[2-[4-[3-(benzyloxy)phenylsulfanyl]-2-chlorophenyl]ethyl]propane-1,3-diol hydrochloride, ((it should be noted that the compound is also referred to as KRP-203, and is also disclosed in WO 2003/029205 A1), Compound 4=1-[4-[N-[4-cyclohexyl-3-(trifluoromethyl)benzyloxy]-1(E)-imino ethyl]-2-ethylbenzyl]azetidine-3-carboxylic acid (it should be noted that the compound is also disclosed in WO 2004/103306 A1), Compound At=5-chloro-N-[(1R)-1-{4-ethyl-5-[3-(4-methylpiperazin-1-yl)phenoxy]-4H-1,2,4-triazol-3-yl}ethyl]naphthalene-2-sulfonamide (it should be noted that the compound is also disclosed in WO 2007/089018 A1 as Compound 120), $S1P_1$ receptor agonist=sphingosine 1-phosphate receptor 1 agonist, $S1P_1$ receptor antagonist=sphingosine 1-phosphate receptor 1 antagonist, and FTY720=2-amino-2-[2-(4-octylphenyl)ethyl]propane-1,3-diol hydrochloride.

In this specification, the "$S1P_1$ receptor agonist" refers to a compound or a pharmaceutically acceptable salt thereof which binds to a $S1P_1$ receptor and which promotes the binding of $GTP[\gamma^{35}S]$ to the receptor. As one embodiment of the $S1P_1$ receptor agonist, there is given a compound having an $EC_{50}$ value for the receptor agonist effect measured by $GTP[\gamma^{35}S]$ binding assay of from 100 μM to 1 μM or a pharmaceutically acceptable salt thereof. As another embodiment of the $S1P_1$ receptor agonist, there is given a compound having the $EC_{50}$ value of from 100 nM to 10 μM or a pharmaceutically acceptable salt thereof. AS still another embodiment of the $S1P_1$ receptor agonist, there is given a compound having the $EC_{50}$ value of from 10 nM to 0.1 nM or a pharmaceutically acceptable salt thereof.

As one embodiment of the $S1P_1$ receptor agonist, FTY720 (WO 1994/008943 A1) is available in the market as a therapeutic agent for multiple sclerosis. FTY720 is phosphorylated by SPHK2, which is a sphingosine kinase, and binds to the $S1P_1$ receptor and then downregulates the $S1P_1$ receptor on lymphocytes. As a result, it is known that the transfer of mature lymphocytes from thymus and secondary lymphoid tissues is inhibited, and that FTY720 exhibits its immunosuppressive action by sequestering mature lymphocytes which circulate in the blood within the secondary lymphoid tissues (YAKUGAKU ZASSHI (Journal of the Pharmaceutical Society of Japan), 2009, 129(6), p. 655-665).

As another embodiment of the $S1P_1$ receptor agonist, there is given, for example, 5(Z)-[3-chloro-4-[2(R),3-dihydroxypropoxy]benzylidene]-3-(2-methylphenyl)-2(Z)-(propylimino)thiazolidin-4-one (ACT-128800, Ponesimod) (WO 2005/054215 A1) or 1-[5-[3-amino-4-hydroxy-3(R)-methylbutyl]-1-methyl-1H-pyrrol-2-yl]-4-(4-methylphenyl) butan-1-one (CS-0777) (WO 2012/073991 A1).

As still another embodiment of the $S1P_1$ receptor agonist, there is given, for example, an oxazolo[4,5-c]pyridinecarboxylic acid derivative (WO 2013/004824 A1), an aminopropylene glycol derivative (WO 2013/004190 A1), a substituted bicyclomethylamine derivative (WO2012/145236A1), a 2-methoxy-pyridin-4-yl derivative (WO 2012/098505 A1), a pyrimidine derivative (WO 2011/113309 A1), or a carboxylic acid derivative having a 2,5,7-substituted oxazolopyrimidine ring (WO 2011/086077 A1).

The following compounds or pharmaceutically acceptable salts thereof are given as specific examples of compounds each serving as the $S1P_1$ receptor agonist: 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof, 1-[(7-{[4-(2,2,2-trifluoroethoxy)-3-(trifluoromethyl)benzyl]oxy}-2H-chromen-3-yl)methyl]piperidine-4-carboxylic acid or a pharmaceutically acceptable salt thereof, 2-amino-2-[2-[4-[3-(benzyloxy)phenylsulfanyl]-2-chlorophenyl]ethyl]propane-1,3-diol or a pharmaceutically acceptable salt thereof, and 1-[4-[N-[4-cyclohexyl-3-(trifluoromethyl)benzyloxy]-1 (E)-imino ethyl]-2-ethylbenzyl]azetidine-3-carboxylic acid or a pharmaceutically acceptable salt thereof.

Another specific example of the $S1P_1$ receptor agonist is Compound 1, Compound 2, Compound 3, or Compound 4, or its hemifumarate.

In this specification, the "$S1P_1$ receptor antagonist" refers to a compound which suppresses an increase in GTP-γS binding which is induced by S1P and the $S1P_1$ receptor agonist, or a pharmaceutically acceptable salt thereof. As one embodiment of the $S1P_1$ receptor antagonist, there is given a compound having an $EC_{50}$ value for the receptor antagonist effect measured by $GTP[\gamma^{35}S]$ binding assay of from 100 μM to 1 μM or a pharmaceutically acceptable salt thereof. As another embodiment of the $S1P_1$ receptor antagonist, there is given a compound having the $EC_{50}$ value of from 100 nM to 10 μM or a pharmaceutically acceptable salt thereof. As still another embodiment of the $S1P_1$ receptor antagonist, there is given a compound having the $EC_{50}$ value of from 10 nM to 0.1 nM or a pharmaceutically acceptable salt thereof. A specific example of the $S1P_1$ receptor antagonist is 5-chloro-N-[(1R)-1-{4-ethyl-5-[3-(4-methylpiperazin-1-yl)phenoxy]-4H-1,2,4-triazol-3-yl}ethyl]naphthalene-2-sulfonamide or a pharmaceutically acceptable salt thereof (WO 2007/089018 A1, Compound 120).

In this specification, specific examples of the "pharmaceutically acceptable salt" include acid addition salts with an inorganic acid, such as hydrochloric acid, hydrobromic acid, hydroiodic acid, sulfuric acid, nitric acid, or phosphoric acid, and an organic acid, such as formic acid, acetic acid, propionic acid, oxalic acid, malonic acid, succinic acid, fumaric acid, hemifumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, or glutamic acid.

In this specification, the "cerebral aneurysm" means an unruptured cerebral aneurysm. In many cases, cerebral aneurysm is caused by the decrease in the strength of blood vessel walls through vascular wall degeneration resulting from the inflammatory reaction due to a load on cerebral artery walls by hemodynamic. In some cases, however, in addition to the above, cerebral aneurysm is caused by arteriosclerosis of cerebral artery, bacterial infection of cerebral artery, head injury, and the like. Cerebral aneurysm is classified into, based on its form and pathoetiology, for example, saccular cerebral aneurysm, which is formed at the cerebral artery bifurcation mainly under a load of hemodynamic stress, fusiform cerebral aneurysm, which is formed by dilatation of cerebral blood vessels themselves as a result of arteriosclerosis, inflammatory cerebral aneurysm, which is caused by bacterial infection and the like, dissecting cerebral aneurysm, which is caused by deterioration, disruption, and the like of internal elastic lamina of an artery, and the like.

In this specification, the "pharmaceutical composition for the inhibition of formation and/or enlargement of cerebral aneurysm or for the regression of cerebral aneurysm" means a pharmaceutical composition for the inhibition of formation of cerebral aneurysm and/or a pharmaceutical composition for the inhibition of enlargement of formed cerebral aneurysm or a pharmaceutical composition for the regression of formed cerebral aneurysm. In one embodiment, the pharmaceutical composition is (i) a pharmaceutical composition for the inhibition of formation of cerebral aneurysm. In another embodiment, the pharmaceutical composition is (ii) a pharmaceutical composition for the inhibition of enlargement of formed cerebral aneurysm. In still another embodiment, the pharmaceutical composition is (iii) a pharmaceutical composition for the regression of formed cerebral aneurysm. By inhibiting formation of cerebral aneurysm and/or by inhibiting enlargement of cerebral aneurysm or by regressing cerebral aneurysm, a disease associated with cerebral aneurysm can be prevented and/or treated. The "disease associated with cerebral aneurysm" is a disease associated with formation and/or enlargement or rupture of cerebral aneurysm. In one embodiment, there is given subarachnoid hemorrhage. In another embodiment, there are given intracerebral hemorrhage, acute subdural hematoma, and the like. In addition, in one embodiment, there are given pressure symptoms of brain (for example, paralysis and impaired consciousness) associated with enlargement of aneurysm, cranial nerve palsy (for example, oculomotor nerve paralysis and optic nerve disorder), and the like.

The pharmaceutical composition of the present invention, which contains a $S1P_1$ receptor agonist as an active ingredient and which is used for the prevention and/or treatment of a disease associated with cerebral aneurysm, is generally prepared by using a carrier and an excipient which are used for drug formulation and other additives. The administration may be any of forms including forms for oral administration such as a tablet, a pill, a capsule, a granule, a powder, and a liquid, and forms for parenteral administration including an injection, such as an intravenous injection, and an intramuscular injection, a suppository, a transdermal preparation, a transnasal preparation, an inhalant, and the like.

A dose is appropriately determined depending on individual cases in consideration of the symptom, and the age, the sex, and the like of the subject to be administrated, while generally, when administered orally, the dose is selected from the range of from 0.001 mg/kg to 100 mg/kg, preferably from 0.003 mg/kg to 0.3 mg/kg per day for an adult human. This amount can be administrated at once or administrated by dividing the amount into two to four doses. In addition, when intravenous administration is employed based on the symptom, generally, the administration is performed one or more times a day in the range of from 0.0001 mg/kg to 10 mg/kg, preferably from 0.003 mg/kg to 0.3 mg/kg per once for a human adult. Further, when inhalation is employed, generally, the administration is performed one or more times a day in the range of from 0.001 mg/kg to 100 mg/kg, preferably from 0.003 mg/kg to 0.3 mg/kg per once for a human adult.

As a solid composition for oral administration according to the present invention, a tablet, a powder, a granule, and the like are employed. In such solid composition, one or more active substances are mixed with at least one inactive excipient, for example, lactose, mannitol, glucose, hydroxypropylcellulose, microcrystalline cellulose, starch, polyvinylpyrrolidone, magnesium aluminometasilicate, and the like. The composition may contain an inactive additive, for example, a lubricant, such as magnesium stearate, a disintegrating agent, such as sodium carboxymethyl starch, and a solubilizing aid according to a conventional method. The tablet or the pill may be coated with a sugar coating, or a coating soluble in stomach or an enteric coating, if necessary.

A liquid composition for oral administration includes an emulsion, a liquid, a suspension, a syrup, an elixir, and the like, and contains a commonly used inactive solvent, for example, purified water and ethanol. The composition may contain a pharmaceutical aid, such as a solubilizer, a wetting agent, and a suspending agent, a sweetening agent, a flavoring agent, a perfume, and an antiseptic agent, in addition to the inactive solvent.

An injection for parenteral administration includes a sterile aqueous or non-aqueous liquid, suspension, and emulsion. An aqueous solvent includes, for example, distilled water for injection and physiological saline. A non-aqueous solvent includes, for example, propylene glycol, polyethylene glycol, a vegetable oil, such as olive oil, alcohols, such as ethanol, polysorbate 80 (the name in the Japanese Pharmacopoeia), and the like. Such composition may further contain an isotonizing agent, an antiseptic agent, a wetting agent, an emulsifying agent, a dispersant, a stabilizing agent, and a solubilizing aid. Such composition is sterilized, for example, by filtration through a bacterial-retaining filter, compounding of a disinfectant, or irradiation. In addition, such composition may be used by preparing a sterile solid composition and then dissolving or suspending the sterile solid composition in sterile water or a sterile injectable solvent before use.

EXAMPLES

In order to understand the present invention deeper, the experimental results leading to the present invention are shown in each of Reference Examples, specific contents of the invention are shown in Examples, and they are described in detail. The present invention is not limited to the matters described in these Reference Examples or Examples.

In this specification, the following abbreviations are used in some cases.
(Abbreviations)
MC=methylcellulose, SD rat=Sprague-Dawley rat, high-salt diet=normal diet containing 0.12% β-aminopropionitrile and 8% sodium chloride, surgery=surgery for inducing cerebral aneurysm, cerebral aneurysm model=rat model which has undergone the surgery for inducing cerebral aneurysm, Day X=X days after the surgery for inducing cerebral aneurysm, with taking the day on which the surgery for inducing cerebral aneurysm was conducted to be Day 0 (for example, the day after the surgery is referred to as Day 1), vehicle group=group without being administered a drug (group administered 0 mg/kg of drug), control group=group which has not undergone the surgery for inducing cerebral aneurysm, ELASTICA VAN GIESON staining=EvG staining.

(Preparation of Suspensions of Compounds)

A "suspension of a $S1P_1$ receptor agonist" was prepared by using a 0.5% MC solution after grinding a $S1P_1$ receptor agonist in a mortar. Herein, the amount of a $S1P_1$ receptor agonist in the setting of a dose refers to an amount equivalent to a free form of the $S1P_1$ receptor agonist. For example, a "suspension of Compound 1" was prepared by using a 0.5% MC solution after grinding Compound 1 in a mortar. Herein, the amount of Compound 1 in the setting of a dose refers to an amount equivalent to a free form of Compound 1.

Reference Example 1

Preparation of Cerebral Aneurysm Model

A rat model of cerebral aneurysm was prepared according to the method disclosed on the literature by Hashimoto et al. (Surgical Neurology 1978, Vol. 10, p. 3-8). Namely, 50 mg/kg of pentobarbital was administrated intraperitoneally to a 7-week-old male SD rat, and the left common carotid artery and the left renal artery were ligated by using 10-0 nylon thread under anesthesia (this is referred to as the surgery for inducing cerebral aneurysm). From the day after surgery (Day 1), the rat was reared with being fed a high-salt diet. During a rearing period, the rat was given free access to water.

Reference Example 2

Expression of $S1P_1$ Receptor in Endothelial Cells at Cerebral Artery Bifurcation Forced oral administration of 0.03 mg/5 mL of a suspension of Compound 1 to the cerebral aneurysm model was conducted once a day at a dose of 5 mL/kg from 1 day after surgery (Day 1) to 27 days after surgery (Day 27).

It should be noted that forced oral administration of the 0.5% MC solution (0 mg/5 mL of the suspension of Compound 1) to the cerebral aneurysm model was conducted once a day at a dose of 5 mL/kg. The group of these rats was defined as a vehicle group.

1) 28 days after surgery (Day 28), the same rat was dissected under deep anesthesia, and blood vessels were transcardially perfused with 4% paraformaldehyde. The brain was extirpated as it is together with blood vessels of the surface of the brain, and was fixed overnight at 4° C. in a phosphate buffer containing 4% paraformaldehyde.
2) Then, the solution was replaced with 30% sucrose solution, and the brain was further left to stand still for 24 hours at 4° C.
3) From the surface of the brain, the right olfactory artery/ anterior cerebral artery bifurcation containing cerebral aneurysm (the bifurcation of right cerebral blood vessels on the side opposite to the side of the obstruction) was extirpated, and a frozen section (with a thickness of 5 μm) was prepared.
4) The frozen section was permeabilized with a phosphate buffer containing 0.3% polysorbate 20 at room temperature for 30 minutes. 5) The section was blocked with a phosphate buffer containing 5% donkey serum at room temperature for 1 hour.
6) As a primary antibody, an anti-$S1P_1$ receptor murine monoclonal antibody (MABC94: Millipore) was diluted with a phosphate buffer by 100 times, and was allowed to react at 4° C. for 72 hours.
7) Then, after washing the section with a phosphate buffer containing 0.3% polysorbate 20, an Alexa 488-conjugated donkey anti-mouse IgG antibody (Invitrogen), as a secondary antibody, was diluted with a phosphate buffer by 100 times and was allowed to react at room temperature for 1 hour.
8) The section was washed with a phosphate buffer containing 0.3% polysorbate 20, and was mounted in a discoloration-preventing agent (Prolong Gold™: Invitrogen).
9) The section was observed with a confocal microscope.

Figure 1:
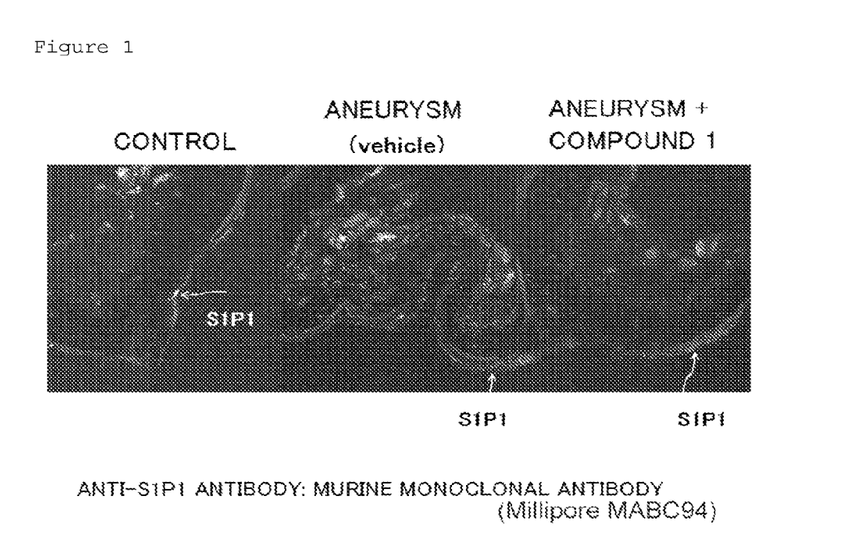
FIG. 1 is a photograph for showing the expression of a $S1P_1$ receptor in endothelial cells at the cerebral artery bifurcation (Reference Example 2).

The results are shown in FIG. 1. It should be noted that a group of rats which did not undergo the surgery for inducing cerebral aneurysm was defined as a control group. In all of the control group, the vehicle group, and the Compound 1 administration group, the expression of the $S1P_1$ receptor was observed in endothelial cells at the cerebral artery bifurcation where cerebral aneurysm was formed.

Reference Example 3

Lymphopenic Action

Forced oral administration of 0.03 mg/5 mL or 0.1 mg/5 mL of the suspension of Compound 1 to the cerebral aneurysm model was conducted once a day at a dose of 5 mL/kg from 1 day after surgery (Day 1) to 27 days after surgery (Day 27).

It should be noted that forced oral administration of the 0.5% MC solution (0 mg/5 mL of the suspension of Compound 1) to the cerebral aneurysm model was conducted once a day at a dose of 5 mL/kg. The group of these rats was defined as a vehicle group.

28 Days after surgery (Day 28), 50 mg/kg of pentobarbital, which was an anesthetic drug, was administrated intraperitoneally to a rat and blood was collected from inferior vena cava under anesthesia. The number of lymphocytes in the collected blood was counted by using a blood test system (Advia 120, Siemens Healthcare Diagnostics) according to the manual of the system.

Figure 2:
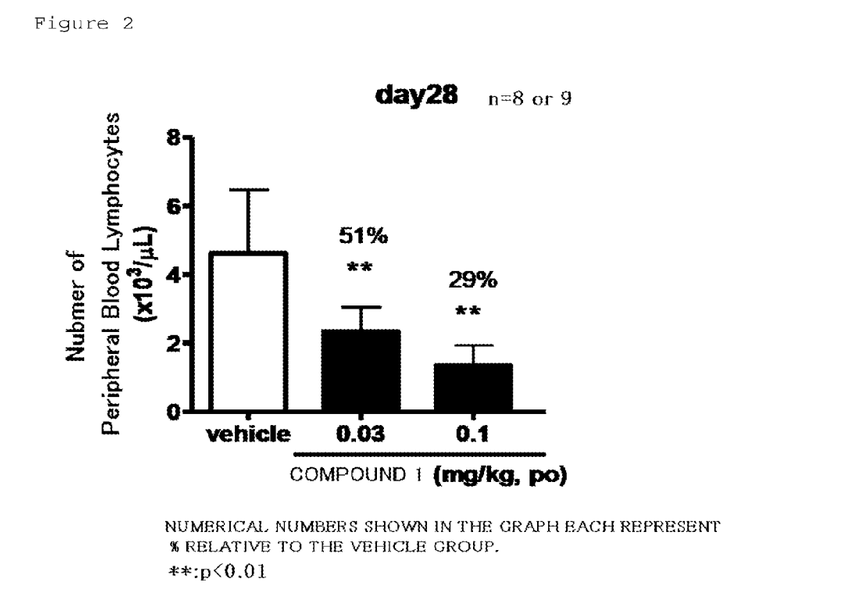
FIG. 2 is a graph for showing a decrease in the number of lymphocytes in peripheral blood by Compound 1 (Reference Example 3).

The results are shown in FIG. 2. Compound 1 decreased the number of lymphocytes in peripheral blood in a concentration-dependent manner. In general, it is known that a $S1P_1$ receptor agonist inhibits the $S1P_1$ receptor-dependent transfer of lymphocytes from secondary lymphoid tissues by inducing downregulation of the $S1P_1$ receptor on lymphocytes. The results shown in FIG. 2 suggest that Compound 1 acts as a $S1P_1$ receptor agonist in rats in vivo.

Reference Example 4

Infiltration of Macrophages into Cerebral Aneurysm Formation Site

Forced oral administration of 0.03 mg/5 mL or 0.1 mg/5 mL of the suspension of Compound 1 to the cerebral aneurysm model was conducted once a day at a dose of 5 mL/kg from 1 day after surgery (Day 1) to 27 days after surgery (Day 27). 28 Days after surgery (Day 28), the treatments on the right olfactory artery/anterior cerebral artery bifurcation containing cerebral aneurysm were conducted by using similar procedures to the steps 1) to 5) of Reference Example 2, and a section of the bifurcation was prepared.

Figure 3A:
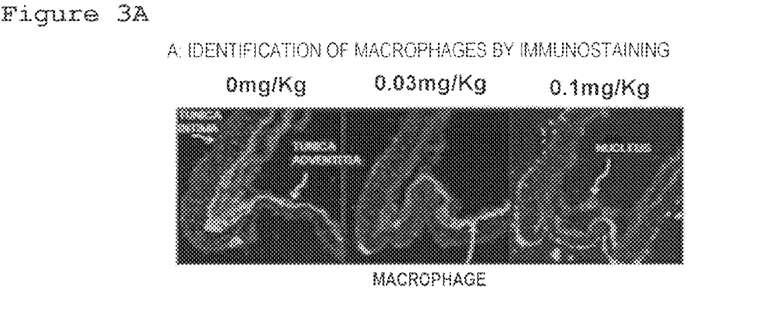
FIG. 3A is a photograph for showing macrophages infiltrating the cerebral artery bifurcation in a cerebral aneurysm model (Reference Example 4).

Immunostaining of macrophages (F4/80-positive cells) was conducted on the prepared section as described below. As a primary antibody solution, a solution in which a rat anti-F4/80 antibody [BM8](AB16911: Abcam) was diluted with a phosphate buffer by 100 times was prepared. As a secondary antibody solution, a solution in which an alexa 488-conjugated donkey anti-rat IgG antibody (Invitrogen) was diluted with a phosphate buffer by 100 times was prepared. The section was allowed to react in the primary antibody solution at 4° C. for 16 hours, washed with a phosphate buffer, and thereafter, was allowed to react in the secondary antibody solution at room temperature for 1 hour. The section was washed with a phosphate buffer, and thereafter, was mounted in a discoloration-preventing agent (ProlongGold™: Invitrogen) and was observed with a confocal microscope. Cell nuclei located in portions of tunica adventitia of cerebral artery were observed to be stained blue (in monochrome FIG. 3A, portions with a relatively low degree of whiteness). In addition, macrophages (F4/80-positive cells) stained green at the peripheries of nuclei (blue) were observed therein (in monochrome FIG. 3A, portions with a higher degree of whiteness).

Figure 3B:
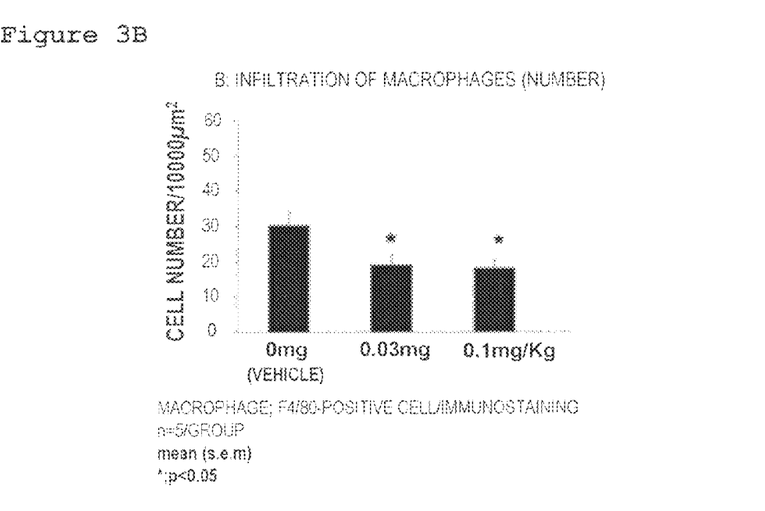
FIG. 3B is a graph for showing a decrease in the number of macrophages infiltrating the cerebral artery bifurcation by Compound 1 (Reference Example 4).

Under the observation with a confocal microscope, the number of macrophages was counted in an area of 100 μm square centered around the cerebrovascular bifurcation where cerebral aneurysm developed. The measurement was conducted on five rats and the mean value was calculated. The results are shown in FIG. 3B. In the case of the vehicle group, the number of macrophages at the cerebral aneurysm formation site was about 30 cells/10000 μm². On the other hand, before the surgery, the number of macrophages at the same site was from 2 cells/10000 μm² to 4 cells/10000 μm². Accordingly, it was confirmed that the number of macrophages in the vehicle group was increased as compared to that before the surgery.

The number of macrophages in each of groups in which Compound 1 was administered at doses of 0.03 mg/kg and 0.1 mg/kg was decreased as compared to the number of macrophages in the vehicle group.

Reference Example 5

Suppression of Expression of MCP-1 by Compound 1

Figure 4:
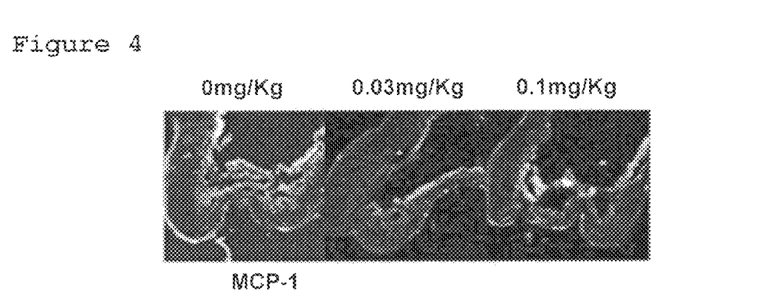
FIG. 4 is a photograph for showing suppression of the expression of MCP-1 at the cerebral artery bifurcation by Compound 1 (Reference Example 5).

A goat anti-MCP-1 antibody (Santa Cruz) was used as a primary antibody, an alexa-488-conjugated anti-goat IgG antibody (Invitrogen) was used as a secondary antibody, and observation with a confocal microscope was conducted by using the method of Reference Example 4. The results are shown in FIG. 4. Shining white portions represent MCP-1. The expression of MCP-1 was confirmed in cerebral aneurysm walls in the vehicle group.

When Compound 1 was administered at doses of 0.03 mg/kg or 0.1 mg/kg, the expression of MCP-1 was suppressed as compared to the group without being administered a drug.

Example 1

Effects of Compound 1 (In Vivo)

(1) Inhibitory Effect of Compound 1 on Formation of Cerebral Aneurysm

Forced oral administration of 0.03 mg/5 mL or 0.1 mg/5 mL of the suspension of Compound 1 to the cerebral aneurysm model was conducted once a day at a dose of 5 mL/kg from the day after surgery, i.e., 1 day after surgery (Day 1) to 27 days after surgery (Day 27).

It should be noted that forced oral administration of the 0.5% MC solution (0 mg/5 mL of the suspension of Compound 1) to the cerebral aneurysm model was conducted once a day at a dose of 5 mL/kg. The group of these rats was defined as a vehicle group.

28 Days after surgery (Day 28), the right olfactory artery/anterior cerebral artery bifurcation containing cerebral aneurysm was extirpated and was fixed with 4% paraformaldehyde, and then the solution was replaced with a 30% sucrose solution, and thereafter, the extirpated bifurcation was frozen to prepare a specimen of a frozen section having a thickness of 5 μm, by similar procedures to the steps 1) and 2) of the method of Reference Example 2. This specimen was subjected to EvG staining and the formation of cerebral aneurysm was confirmed. The size of cerebral aneurysm was measured and evaluation was conducted. The maximum diameter (Maximum) represents the maximum distance between internal elastic lamina disruption sites observed by EvG staining, the height "Height" represents the maximum value of height defined as the length of the perpendicular line drawn from the line connecting the two ends of internal elastic lamina, and the mean diameter "Mean" represents the mean value of the maximum diameter and the height. This evaluation was conducted on all the rats (8 or 9 rats) of each of the groups, and the mean value of each of the groups was calculated.

Figure 5:
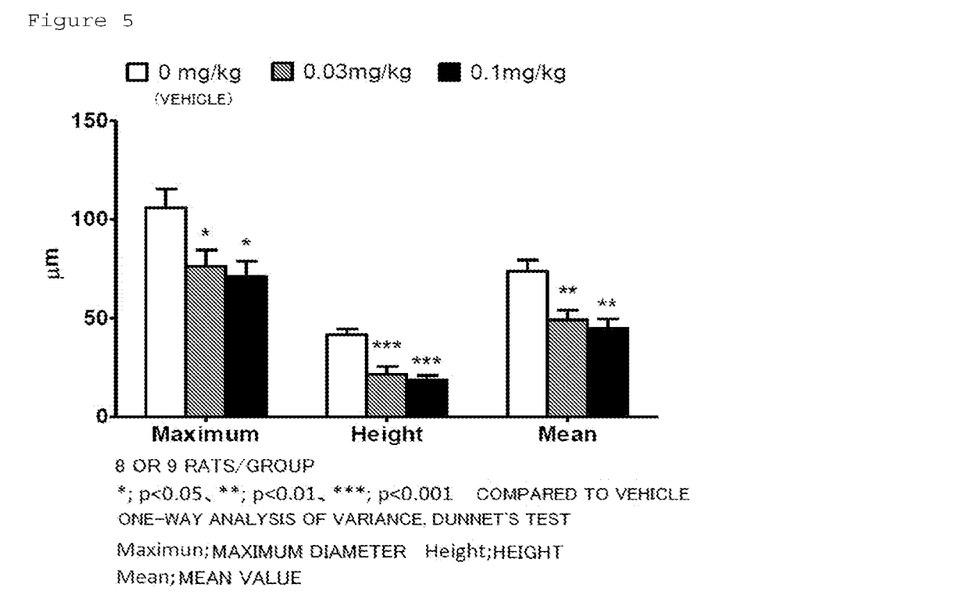
FIG. 5 is a graph for showing an inhibitory effect of Compound 1 on formation of cerebral aneurysm in a cerebral aneurysm model (Example 1).
Figure 6:
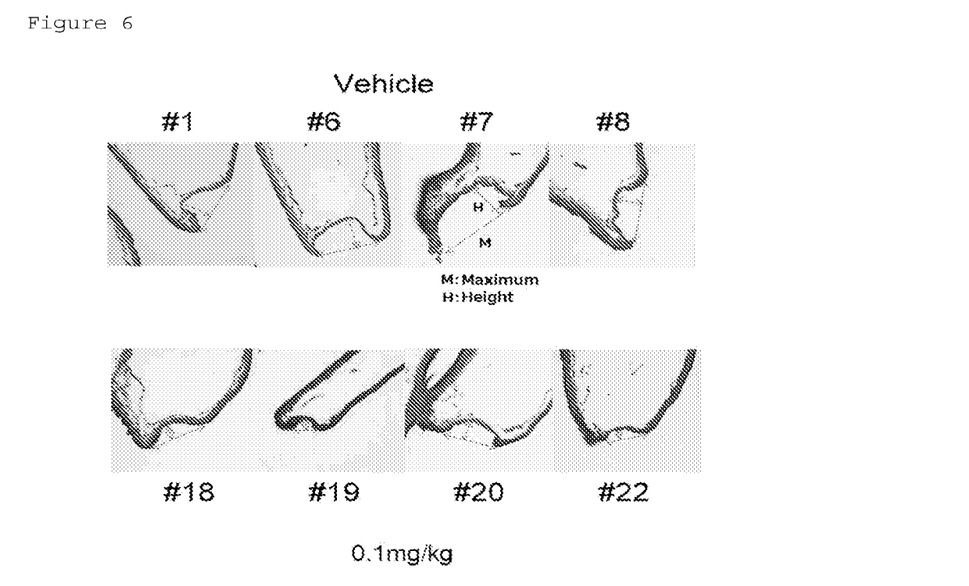
FIG. 6 is a photograph of EvG-stained frozen thin sliced specimens containing a portion of cerebral aneurysm of Example 1 (Example 1).

The results are shown in FIG. 5. Compound 1 inhibited the formation of cerebral aneurysm. Examples of stained specimens are shown in FIG. 6. The size of a line connecting two ends of internal elastic lamina at the bottom of cerebral aneurysm shown by the bidirectional arrow and the height in the perpendicular direction from the bottom were measured. The largest size between two ends of internal elastic lamina was defined as "Maximum", and the portion with the highest aneurysm was defined as "Height".

(2) Influences of Compound 1 on Blood Pressure and Heart Rate of Rats

Figure 7:
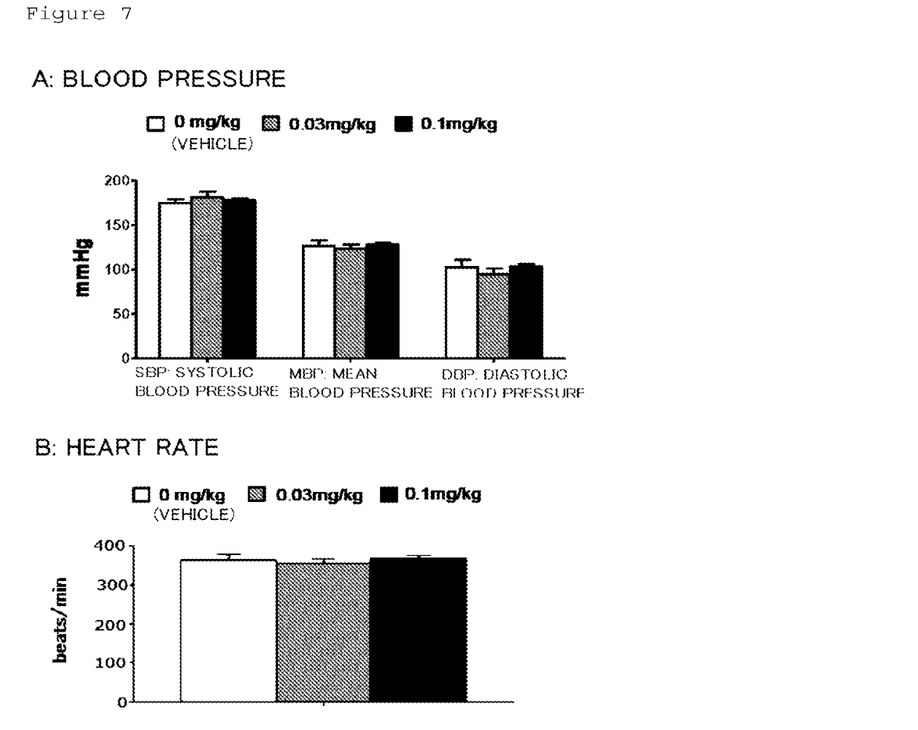
FIG. 7 is a graph for showing influences of Compound 1 on blood pressure and heart rate (Example 1).

Immediately before dissecting rats 28 days after surgery (Day 28) as described in the section (1) of Example 1, blood pressure and heart rate of each of rats were measured noninvasively without anesthesia by a tail-cuff method. The measurement was conducted by using a noninvasive blood pressure measuring device for rats and mice BP-98A (Softron). The measurement was conducted three times per rat, and the mean value was used for calculating the mean value of all rats in each of the groups. The results are shown in FIG. 7A and FIG. 7B. No influence of the administration of Compound 1 on any blood pressure (SBP: systolic blood pressure, MBP: mean blood pressure, DBP: diastolic blood pressure) or heart rate was observed.

Example 2

Inhibitory Effects of Compound 1 on Enlargement of Cerebral Aneurysm (In Vivo)

The cerebral aneurysm model was reared with being fed a high-salt diet for 7 days from the day of the surgery so that the model formed cerebral aneurysm. 7 Days after surgery (Week 1, Day 7), the diet for the cerebral aneurysm model was replaced with a normal diet, and forced oral administration of the suspension of Compound 1 at a concentration of 0.1 mg/5 mL to the cerebral aneurysm model was conducted once a day.

It should be noted that forced oral administration of the 0.5% MC solution (0 mg/5 mL of the suspension of Compound 1) to the cerebral aneurysm model was conducted once a day at a dose of 5 mL/kg. The group of these rats was defined as a vehicle group.

Figure 8:
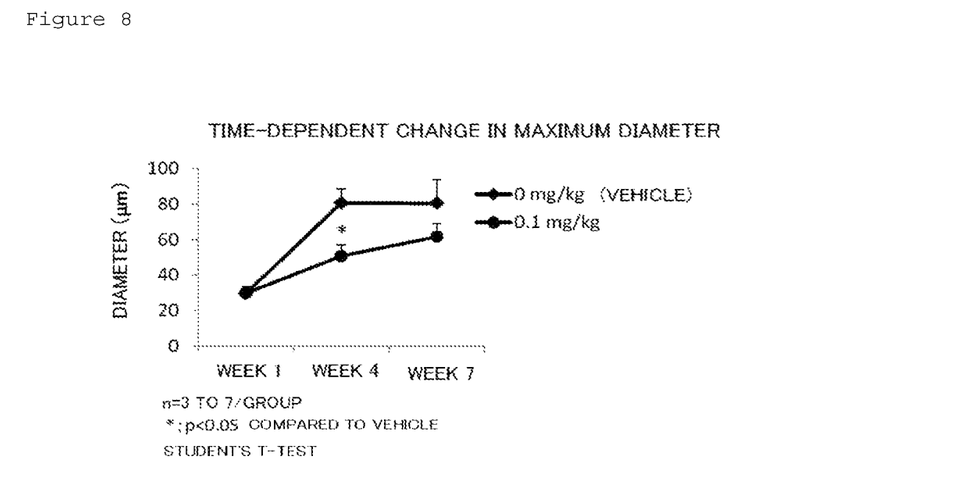
FIG. 8 is a graph for showing an inhibitory effect of Compound 1 on enlargement of cerebral aneurysm (time-dependent change in the maximum diameter of cerebral aneurysm) (Example 2).
Figure 9:
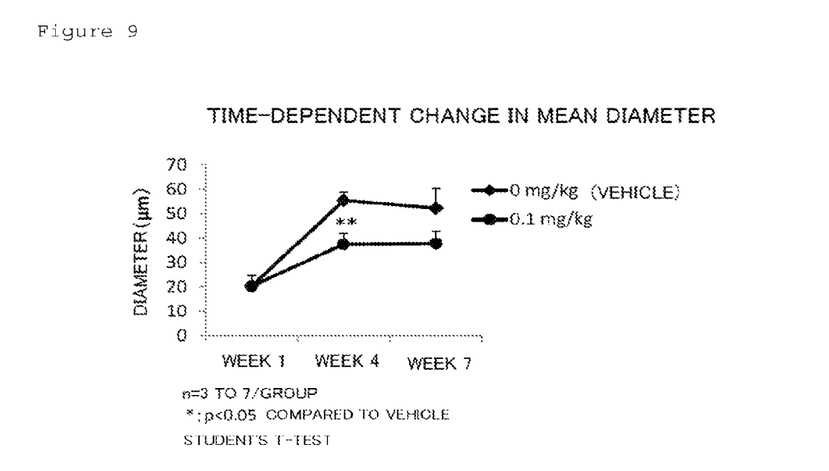
FIG. 9 is a graph for showing an inhibitory effect of Compound 1 on enlargement of cerebral aneurysm (time-dependent change in the mean diameter of cerebral aneurysm) (Example 2).

7 Days after surgery (Week 1, Day 7), 28 days after surgery (Week 4, Day 28), and 49 days after surgery (Week 7, Day 49), the right olfactory artery/anterior cerebral artery bifurcation containing cerebral aneurysm was extirpated and the size of cerebral aneurysm (the maximum diameter and the mean diameter) was measured by similar procedures to Example 1. The results are shown in FIG. 8 and FIG. 9. Compound 1 inhibited the enlargement of cerebral aneurysm.

Figure 10:
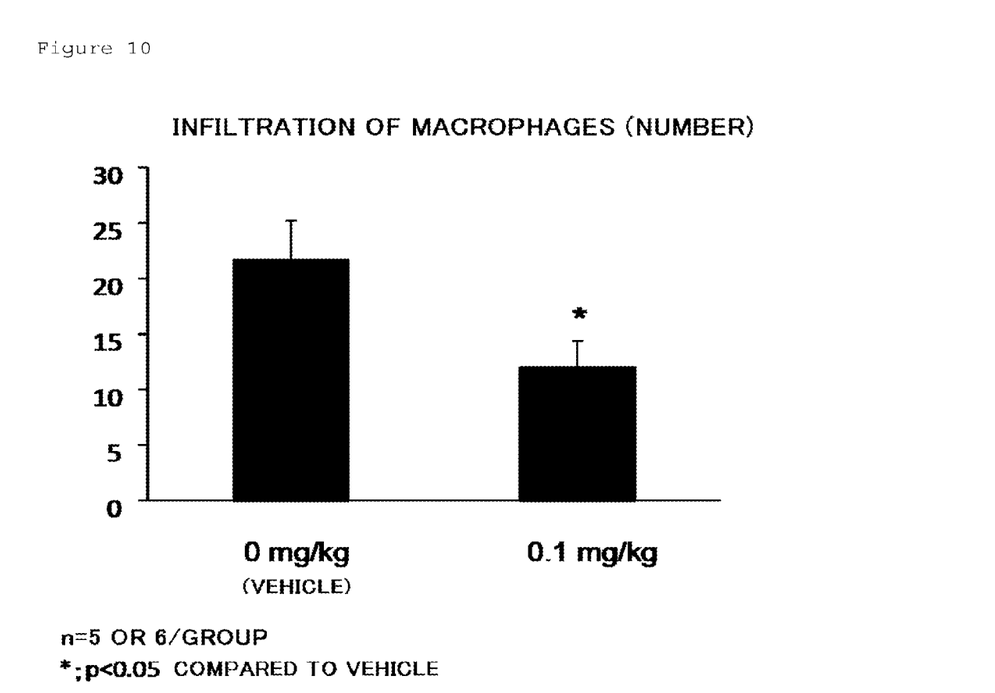
FIG. 10 is a graph for showing a decrease in the number of macrophages infiltrating cerebral aneurysm walls by Compound 1 (Example 2).

In addition, 49 days after surgery (Week 7), the number of macrophages infiltrating cerebral aneurysm walls was counted according to the procedure of Reference Example 4 under the observation with a confocal microscope. The results are shown in FIG. 10. Compound 1 decreased the number of macrophages at the site where cerebral aneurysm was induced.

Example 3

Inhibitory Effect of Compound 2 on Formation of Cerebral Aneurysm

Figure 11:
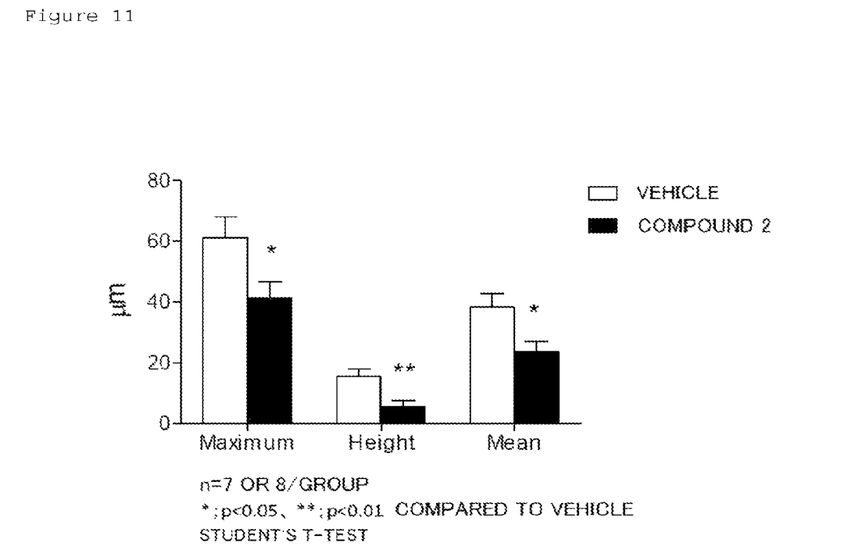
FIG. 11 is a graph for showing an inhibitory effect of Compound 2 on formation of cerebral aneurysm (Example 3).

The administration of 0.1 mg/5 mL of a suspension of Compound 2 to the cerebral aneurysm model was started on the day of the surgery (Day 0) at a dose of 5 mL/kg, and forced oral administration was conducted once a day until 26 days after surgery (Day 26). The size of cerebral aneurysm was measured by using the protocol of Example 1. The results are shown in FIG. 11. Compound 2 inhibited the formation of cerebral aneurysm.

Example 4

Inhibitory Effect of Compound 3 on Formation of Cerebral Aneurysm

Figure 12:
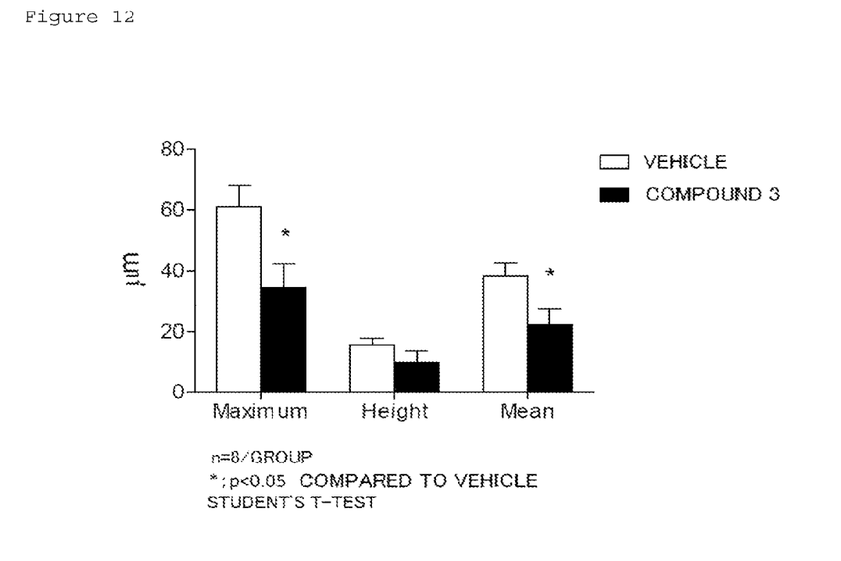
FIG. 12 is a graph for showing an inhibitory effect of Compound 3 on formation of cerebral aneurysm (Example 4).

The administration of 0.01 mg/5 mL of a suspension of Compound 3 to the cerebral aneurysm model was started on the day of the surgery (Day 0) at a dose of 5 mL/kg, and forced oral administration was conducted once a day until 26 days after surgery (Day 26). The size of cerebral aneurysm was measured by using the protocol of Example 1. The results are shown in FIG. 12. Compound 3 inhibited the formation of cerebral aneurysm.

Example 5

Inhibitory Effect of Compound 4 on Formation of Cerebral Aneurysm

Figure 13:
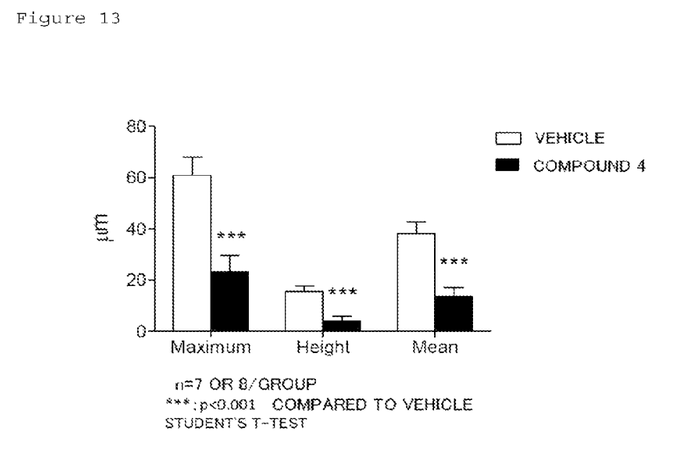
FIG. 13 is a graph for showing an inhibitory effect of Compound 4 on formation of cerebral aneurysm (Example 5).

The administration of 0.3 mg/5 mL of a suspension of Compound 4 to the cerebral aneurysm model was started on the day of the surgery (Day 0) at a dose of 5 mL/kg, and forced oral administration was conducted once a day until 26 days after surgery (Day 26). The size of cerebral aneurysm was measured by using the protocol of Example 1. The results are shown in FIG. 13. Compound 4 inhibited the formation of cerebral aneurysm.

Example 6

Inhibitory Effects of Compound 1 on Permeability of Endothelial Cells

Figure 14:
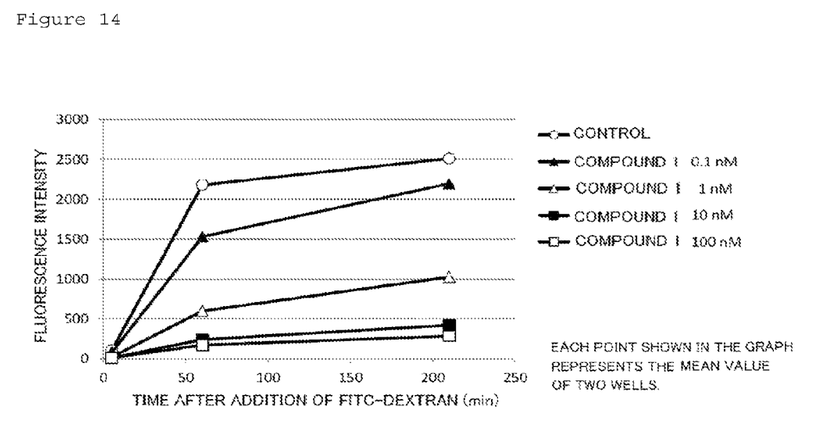
FIG. 14 is a graph for showing a time-dependent change in permeability of endothelial cells caused by the use of Compound 1 (Example 6).

Human carotid artery endothelial cells HCtAEC (Cell Applications) were seeded in the upper compartment of Transwell (diameter: 6.5 mm, pore size: 0.4 µm, collagen-Coated: Corning) so that the cell density was $1 \times 10^5$ cells/well, and the cells were cultured overnight in MesoEndo Growth Medium (Cell Applications) under a 5% $CO_2$ atmosphere at 37° C. The medium was replaced with Endothelial Cell Serum-Free Defined Medium (Cell Applications), and the cells were further cultured overnight under the $CO_2$ atmosphere at 37° C. Then, Compound 1 was added to the upper compartment and the lower compartment of Transwell so that the final concentration was 0 nM, 0.1 nM, 1 nM, 10 nM, or 100 nM, and the cells were cultured continuously. The well to which Compound 1 was not added was defined as a control. After culturing for 60 minutes, 250 µg/mL of fluorescein isothiocyanate (FITC)-dextran (2,000 kDa: Sigma-Aldrich) was added to the upper compartment of Transwell, and the amount of FITC-dextran which permeated into the lower compartment was determined by measuring the fluorescence intensity of the medium in the lower compartment after 5 minutes, 60 minutes, and 210 minutes. The results are shown in FIG. 14. Compound 1 decreased the amount of FITC-dextran which permeated into the lower compartment in a concentration-dependent manner.

This indicates that Compound 1 inhibited permeability among endothelial cells.

Example 7

Inhibitory Actions of $S1P_1$ Receptor Antagonist on Inhibitory Effect of Compound 1 on Permeability of Endothelial Cells Human carotid artery endothelial cells were cultured in a similar manner to Example 6. Then, Compound 1 at a concentration of 0 nM or 100 nM and a S1P₁ receptor antagonist at a concentration of 0 nM, 0.1 nM, 1 nM, 10 nM, or 100 nM were added to the upper compartment of Transwell, and the cells were cultured continuously. The well to which none of Compound 1 and the S1P₁ receptor antagonist was added was defined as a control. Compound At was used as the S1P₁ receptor antagonist.

Figure 15:
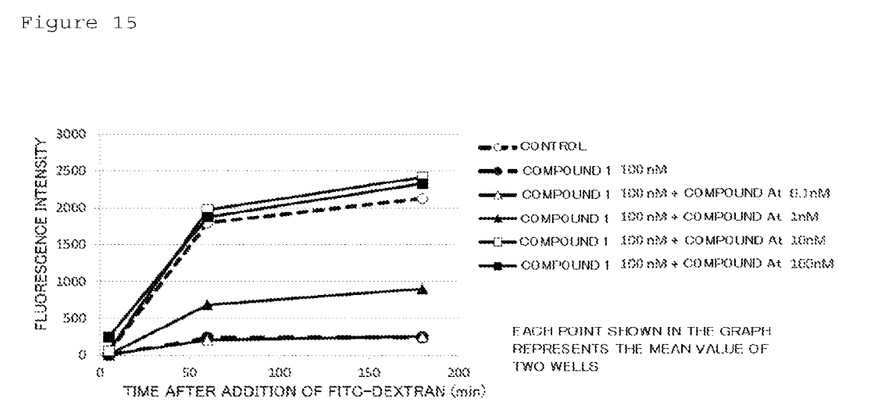
FIG. 15 is a graph for showing a time-dependent change in permeability of endothelial cells caused by the combined use of Compound 1 and a $S1P_1$ receptor antagonist (Example 7)

After culturing for 60 minutes, the amount of FITC-dextran which permeated into the lower compartment was determined in a similar manner to Example 6. The results are shown in FIG. 15. It was confirmed that the S1P₁ receptor antagonist inhibited the inhibitory effect of Compound 1 on permeability of endothelial cells in a concentration-dependent manner.

Accordingly, it was found that the inhibitory effect of Compound 1 on permeability of endothelial cells was an effect mediated by the S1P₁ receptor.

INDUSTRIAL APPLICABILITY

The pharmaceutical composition for the inhibition of formation and/or enlargement of cerebral aneurysm or for the regression of cerebral aneurysm of the present invention, which includes a S1P₁ receptor agonist as an active ingredient, enables inhibition of formation and/or enlargement of cerebral aneurysm or regression of cerebral aneurysm, and enables prevention and/or treatment of a disease associated with cerebral aneurysm.

The invention claimed is:

1. A method for treatment of a disease associated with cerebral aneurysm, comprising administering to a subject in need thereof an effective amount of a sphingosine-1-phosphate receptor 1 agonist which is at least one compound selected from the group consisting of 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof, 1-[(7-{[4-(2,2,2-trifluoroethoxy)-3-(trifluoromethyl)benzyl]oxy}-2H-chromen-3-yl)methyl]piperidine-4-carboxylic acid or a pharmaceutically acceptable salt thereof, 2-amino-2-[2-[4-[3-(benzyloxy)phenylsulfanyl]-2-chlorophenyl]ethyl]propane-1,3-diol or a pharmaceutically acceptable salt thereof, and 1-[4-[N-[4-cyclohexyl-3-(trifluoromethyl)benzyloxy]-1(E)-iminoethyl]-2-ethylbenzyl]azetidine-3-carboxylic acid or a pharmaceutically acceptable salt thereof.

2. The method for treatment according to claim 1, wherein said sphingosine-1-phosphate receptor 1 agonist is 5-{5-[3-(trifluoromethyl)-4-{[(2S)-1,1,1-trifluoropropan-2-yl]oxy}phenyl]-1,2,4-oxadiazol-3-yl}-1H-benzimidazole or a pharmaceutically acceptable salt thereof.

3. The method for treatment according to claim 1, wherein said disease associated with cerebral aneurysm is a disease associated with formation of cerebral aneurysm, enlargement of cerebral aneurysm, or rupture of cerebral aneurysm.

4. The method for treatment according to claim 1, wherein said disease associated with cerebral aneurysm is subarachnoid hemorrhage.

* * * * *